(12) United States Patent
Hirashima et al.

(10) Patent No.: US 7,704,951 B2
(45) Date of Patent: Apr. 27, 2010

(54) METHOD FOR AMELIORATING DYSKINESIA

(75) Inventors: Masaki Hirashima, Kumamoto (JP);
Takumi Sasaki, Kumamoto (JP);
Takeshi Naruse, Kumamoto (JP);
Hiroaki Maeda, Kumamoto (JP);
Chikateru Nozaki, Kumamoto (JP)

(73) Assignee: Juridical Foundation the Chemo-Sero-Therapeutic Research Institute, Kumamoto-shi (JP)

(*) Notice: Subject to any disclaimer, the term of this patent is extended or adjusted under 35 U.S.C. 154(b) by 0 days.

(21) Appl. No.: 12/081,991

(22) Filed: Apr. 24, 2008

(65) Prior Publication Data

US 2009/0075865 A1 Mar. 19, 2009

Related U.S. Application Data

(62) Division of application No. 10/472,444, filed as application No. PCT/JP01/07525 on Aug. 31, 2001, now abandoned.

(30) Foreign Application Priority Data

Mar. 23, 2001 (JP) ............................. 2001-084050

(51) Int. Cl.
*A61K 38/02* (2006.01)
*A61K 38/18* (2006.01)
*A61K 31/095* (2006.01)

(52) U.S. Cl. ......................................... 514/12; 514/706
(58) Field of Classification Search ...................... None
See application file for complete search history.

(56) References Cited

U.S. PATENT DOCUMENTS 4,977,244 A 12/1990 Muchmore et al.

7,199,097 B1 4/2007 Hirashima et al.
2005/0143310 A1 6/2005 Hirashima et al.
2005/0143311 A1 6/2005 Hirashima et al.
2005/0281808 A1 12/2005 Hirashima et al.

FOREIGN PATENT DOCUMENTS

| EP | 0-345-247 A2 | 12/1989 |
| EP | 1-132-402 | 9/2001 |
| WO | WO-00/31131 | 6/2000 |

OTHER PUBLICATIONS

NCBI locus A47327, Sep. 15, 2000.
T. Berry; Medical Hypotheses, vol. 43, 1994, pp. 409-414.
Jun Yan et al.; Journal of Neuroscience, vol. 18, No. 21, Nov. 1, 1998, pp. 8682-8691.
Volker Mostert; Archives of Biochemistry and Biophysics, vol. 376, No. 2, Apr. 15, 2000, pp. 433-438.
Yoshiro Saito et al.; Journal of Health Science, vol. 46, No. 6, pp. 409-413, 2000.
Mostert, "Selenoprotein P: Properties, Functions and Regulation,"vol. 376, No. 2, pp. 433-438 (2000).
Yan et al., "Purification from Bovine Serum of a Survival-Promoting Factor and for Cultured Central Neurons and Its Identification as Selenoprotein-P," vol. 18, No. 21, pp. 6682-8691 (1998).

*Primary Examiner*—Daniel E. Kolker
(74) *Attorney, Agent, or Firm*—Birch, Stewart, Kolasch & Birch, LLP

(57) ABSTRACT

A novel medicament for treating neurodegenerative diseases, especially for ameliorating dyskinesia, comprising as an active ingredient selenoprotein P and/or a peptide fragment or a series of peptide fragments derived from said protein is provided. The novel medicament for treating neurodegenerative diseases, especially for ameliorating dyskinesia, according to the present invention is suitably applicable to diseases with decrease in motor function.

9 Claims, 3 Drawing Sheets

METHOD FOR AMELIORATING DYSKINESIA

This application is a Divisional of application Ser. No. 10/472,444 filed on Sep. 23, 2003 now abandoned and for which priority is claimed under 35 U.S.C. § 120. application Ser. No. 10/472,444 is the national phase of PCT International Application No. PCT/JP01/07525 filed on Aug. 31, 2001 under 35 U.S.C. § 371. The entire contents of each of the above-identified applications are hereby incorporated by reference.

TECHNICAL FIELD OF THE INVENTION

The present invention relates to a novel use of plasma proteins, belonging to the field of medical drugs. More specifically, the present invention relates to a medicament for treating neurodegenerations caused by cell death or cellular degeneration of the cells consisting of the nervous system, such as aging, trauma, cerebrovascular disorders, immunopathy, ataxia, epilepsy, motor neuron disorders, and the like. Still more specifically, the present invention relates to a medicament for treating neurodegenerative disorders, especially for dyskinesia, comprising as an active ingredient selenoprotein P, one of plasma proteins, more preferably a peptide fragment or a series of peptide fragments derived from the C-terminal of selenoprotein P.

BACKGROUND OF THE INVENTION

Neural diseases, where cell death or cellular degeneration of the cells consisting of the nervous system such as neurocytes or glia cells are involved, include cerebrovascular disorders including cerebral infarction, cerebral hemorrhage, subarachnoid hemorrhage, multi-infarct dementia, Binswanger type leukoencephalopathy, and chronic subdural hematoma; autoimmune diseases including multiple sclerosis, Guillain-Barré syndrome, and collagen disease; neurodegenerative diseases including spinocerebellar degeneration, Shy-Drager syndrome, amyotrophic lateral sclerosis, Alzheimer disease, Pick disease, Huntington chorea, Parkinson disease, progressive supranuclear palsy, epilepsy, and Prion disease; dementia or dysbasia associated with aging, or traumatic injury of spinal chord or cerebral disorders due to traffic accident. Among most of these diseases is commonly observed decrease in motor function (dyskinesia).

Dyskinesia includes muscular disorders, neural disorders, and disorders in bones and joints. Among these, central neural disorders leading to dyskinesia is classified according to the regions suffered into cerebral (frontal lobe), cerebellar, vestibular (labyrinth), and spinal dyskinesia.

Cerebral dyskinesia is caused by disorder in cerebral cortex, especially the frontal lobe, and can be observed in case of cerebrovascular lesion, cerebral atrophy, trauma, tumor, Pick disease, and chronic subdural hematoma. It exhibits atactic abasia and decrease in mental function.

Cerebellar dyskinesia is a significant symptom associated with, for instance, cerebellar disorders such as cerebellar tumor, vascular disorders, degenerative disorders, cerebellar atrophy, or deformity. Lesions in the vermis induce trunk ataxia, exhibits astasia-abasia, and gluteus maximus gait, yields difficulty in maintaining posture and position with disorder in balance. On the other hand, disorders in the cerebellar hemisphere exhibit abnormality of tonus in limb muscles and decrease in myotony and are accompanied by maldispositional gait towards the affected lateral direction, incoordination, wrong indication in finger-finger test or finger-nose test, dysmetria, Holmes-Stewart phenomenon, as well as intention tremor and cerebellar speech (scanning, explosive).

Vestibular (labyrinth) ataxia is caused by vestibular malfunctions and most of its cause is supposed to be the presence of, or sequela from, otological disorders in the internal ear, including, for instance, Ménière disease, sudden deafness, disorders in the balance-related nerves due to drug poisoning such as streptomycin or kanamycin, trauma, syphilis, acoustic trauma hearing loss, otosclerosis, and otitis interna (and its sequela).

In case of spinal dyskinesia, also called ataxia of posterior funiculus, disorders in posterior column of spinal cord lead to disorders in bathyesthesia, i.e. positional sensibility, articular sensibility and sensibility of grasp, resulting in ataxia. It is markedly observed in Friedreich's ataxia, subacute combined degeneration of spinal cord, locomotor ataxia, and the like.

These neurodegenerative diseases with dyskinesia are deeply related with cell death or cell degeneration of the neurocytes in their pathological conditions. For example, in case of poly(glutamic acid) disease, observed in Huntington disease, spinocerebellar degeneration (Machado-Joseph disease, Friedreich's ataxia, etc.) or myotonic dystrophy, or Alzheimer disease, cell death and cell degeneration of the neurocytes due to intracellular accumulation of abnormal proteins is observed. For motor neuronal disorders, typically amyotrophic lateral sclerosis, its cause is thought to be cell death of the neurocytes due to generation of free radicals or excessive accumulation of glutamic acid, increase in intracellular calcium ion level, or generation of NO. In case of Parkinson disease, its principal cause is thought to be degeneration of dopaminergic neurocytes in the stratum compacta of substantia nigra.

As the aging process proceeds, man's physical function continually deteriorates. As a morphological basis of the aging process, organs exhibit atrophy (i.e. decrease in weight). For example, the proceedings of the aging process render the brain atrophic, in its extremity resulting in gait disability or dementia. From histopathological point of view, there are observed degeneration or drop-off of the neurocytes, senile plaques, or change in Alzheimer fibril. Cell death or cellular degeneration of the nervous system is supposed to be induced by oxidative stress such as free radicals or glycation. It is also reported that biochemical observation of the brain autopsy revealed decrease in neurotransmitters, especially disturbance of cholinergic neurons, but the cause still remains to be elucidated.

Even if under healthy conditions, a man can fall into gait disability through injury of the spinal cord or the brain by, for instance, traffic accident. When a strong external pressure is applied in case of accidents, dislocation fracture of the spinal column occurs to press the spinal cord or to cause fractural injury in the spinal cord, resulting in injury of the spinal cord. Other causes include radiation burn, incised wound, or stab wound. It can also occur in case where wound is unobservable in bone as is often seen in hyperextension injury of the cervical vertebrae in which detrition and pressure lesion of the spinal cord is observed with marked hemorrhage and edema in parenchyma of the spinal cord. Its clinical symptom includes incomplete or complete systemic paralysis.

Autoimmune diseases are also sometimes accompanied by dyskinesia. Immune system ordinarily acts as a protective mechanism of the living body against a substance foreign and harmful to the host that invades from the environment into the living body. However, the system may sometimes act unfavorably against the living body. When this results in pathological conditions, it is called autoimmune diseases. Diseases exhibiting dyskinesia due to the autoimmune reaction include, for example, myasthenia gravis, multiple sclerosis, and rheumatoid arthritis.

Among these, multiple sclerosis, a kind of demyelination diseases, is characterized by the presence of a variety of demyelination nests of various sizes dispersed within the white matter of the central nervous system with varied lesions of old and new. The lesions are preferentially observed in the white matter such as the periphery of the lateral ventricle, the optic nerve, the brain stem or the spinal cord. Histologically, it is a disease where oligodendrocytes, engaged in formation of medullary sheath, are injured and a large number of oligodendrocytes are observed to have undertaken apoptosis in the lesions. The demyelination nests exhibit at early stage inflammatory infiltration of the cells, which are subsequently consolidated upon replacement with glial fiber at chronic stage. Its clinical symptoms include a various combination of symptoms such as optic neuritis, multiple vision, ocular motor disturbance such as nystagmus, spastic paralysis, painful tonic seizure, Lhermitte syndrome, ataxia, mogilalia and vesicorectal disturbance, where remission is often observed.

In case of cerebrovascular disorders, ischemic conditions in the brain induced by various causes such as cerebral infarction or intracerebral hemorrhage bring about oxygen lack and nutritional disturbance to the cells and tissues in the ischemic region. The oxygen lack first provides with functional impairment via blockage of ATP production, then leads to degeneration, necrosis or atrophy. Specifically, decrease in oxygen and glucose provisions due to ischemia triggers generation of free radicals, excess accumulation of glutamic acid, increase in intracellular calcium ion level, and enhancement of NO production, eventually resulting in death of neurocytes. The ischemic disturbance depends on the duration of ischemia such that the longer the duration of ischemia is, the more exacerbated the reperfusion injury becomes. With these reasons, cell death or cellular degeneration of neurocytes can be the cause of dyskinesia.

As stated above, neurodegenerative diseases with dyskinesia exhibit cell death or cellular degeneration of neurocytes as a common pathology although they may include various diseases. Therefore, any substance that may inhibit or ameliorate cell death or cellular degeneration of neurocytes would be considered to be an effective medicament for treating neurodegenerative diseases, especially dyskinesia. At present, for ameliorating these symptoms, a variety of medical drugs have been proposed, including, for example, a substance that prevents or controls oxidative disturbance in oxidases in the living body such as superoxide dismutase, catalase, or glutathione peroxidase, as well as clinically used medicaments such as trimetazidine hydrochloride, a medicament for treating ischemic heart disease; sodium oxagrel, thromboxane synthetase inhibitor; ifenprodil tartrate, a medicament for improving cerebral circulation and metabolism; and nizofenone fumarate, a medicament for improving ischemic encephalopathy. However, these medicaments cannot entirely inhibit dyskinesia.

As such, little medicament is known for effectively ameliorating symptoms in dyskinesia associated with cell death or cellular degeneration of neurocytes and hence symptomatic treatment has principally been employed. Thus, for instance, a medicament for treating Parkinson disease is used for parkinsonism such as tremor in hands, or an autonomic drug for autonomic symptoms such as orthostatic hypotension. Accordingly, for ameliorating dyskinesia induced by cell death or cellular degeneration of neurocytes, a substance is desired that can inhibit cell death or cellular degeneration generated under disadvantageous conditions for the neurocytes, especially a substance that can elevate anti-oxidative capacity of the cells.

The explanation mentioned above is described by reference to "Why cells die due to ischemia" by Kunio Tagawa, Kyoritsu Publishers Co., Ltd.; "Handbook of stroke" by Keiji Sano, I.P.C.; "Current Diagnosis and Treatment", CD-ROM, Igaku-Shoin Ltd.; "Grand Medical Dictionary", CD-ROM, Nanzando Co., Ltd.; "Up-to-date Grand Medical Dicitionary", CD-ROM, 2nd Ed., Ishiyaku Publishers, Inc.; and "Apoptosis and Diseases", Ed. by Yoshikuni Mizuno, Iyaku (Medicine and Drug) Journal Co., Ltd.

DISCLOSURE OF THE INVENTION

Under the circumstances, the present inventors have found that selenoprotein P, a protein derived from blood components, more preferably a peptide fragment from the C-terminal of selenoprotein P, exhibits a cell death-inhibitory activity, which hitherto has not been reported, and have filed a patent application (PCT/JP99/06322) for this finding. The present inventors further investigated for providing a novel medicament for ameliorating neurodegenerative diseases, especially for ameliorating dyskinesia. As a result, selenoprotein P or a peptide fragment or a series of peptide fragments derived from the C-terminal of selenoprotein P surprisingly proved to be efficacious as a medicament for ameliorating dyskinesia in humans or other animals as demonstrated in animal models which received in vivo administration thereof. Based on this finding, the present inventors have thus completed the present invention.

That is, the present invention relates to a medicament for ameliorating dyskinesia comprising as an active ingredient selenoprotein P and/or a peptide fragment or a series of peptide fragments derived from the C-terminal of selenoprotein P.

In a preferable embodiment of the present invention, the peptide fragment or a series of the peptide fragments from the C-terminal of selenoprotein P is one having the amino acid sequence consisting of 103 amino acid residues from the C-terminal of selenoprotein P, or having said amino acid sequence with one or several amino acid residues therein being deleted, substituted or added, or having a partial sequence of either of the above amino acid sequences, or having any of the above amino acid sequences as a part of a whole sequence.

In a more preferable embodiment of the present invention, the peptide fragment or a series of the peptide fragments from the C-terminal of selenoprotein P has the amino acid sequences of the formula (I):

```
                                          (SEQ ID NO: 1)
Lys Arg Cys Ile Asn Gln Leu Leu Cys Lys Leu Pro

Thr Asp Ser Glu Leu Ala Pro Arg Ser Xaa Cys Cys

His Cys Arg His Leu
``` and/or the formula (II):

```
                                          (SEQ ID NO: 2)
Thr Gly Ser Ala Ile Thr Xaa Gln Cys Lys Glu Asn

Leu Pro Ser Leu Cys Ser Xaa Gln Gly Leu Arg Ala

Glu Glu Asn Ile
``` wherein Xaa represents selenocysteine, or said amino acid sequences with one or several amino acid residues therein being deleted, substituted or added, or a partial sequence of either of the above amino acid sequences, or an amino acid sequence comprising as a part any of the above amino acid sequences.

BEST MODE FOR CARRYING OUT THE INVENTION

Selenoprotein P was identified in 1977 as a selenium-containing protein other than glutathione-peroxidase. In 1982, it was revealed that selenium was incorporated into said protein in the form of selenocysteine. Moreover, in 1991, a full-length amino acid sequence of selenoprotein P was determined by cloning selenoprotein P cDNA and, as a result, possibility that said protein contains at most ten selenocysteine residues was demonstrated (Hill K. E. and Burk R. F., Biomed. Environ. Sci., 10, p. 198-208 (1997)). Little was known about the function of selenoprotein P. However, it has recently been demonstrated that selenoprotein P exhibits an activity to reduce phospholipid hydroperoxide or peroxynitrite in vitro and acts as a survival promoting factor of neurocytes.

As demonstrated in the Examples hereinbelow, selenoprotein P proved to have an activity to ameliorate dyskinesia as it markedly recovered capacity of locomotion in Klotho mice, a mouse model of aging, and also exhibited an effect to inhibit onset of multiple sclerosis as well as to decrease symptoms of said disease in an experimental allergic encephalomyelitis (EAE), a model of multiple sclerosis. It was also shown that selenoprotein P was efficacious for neurological symptoms after ischemia/reperfusion, especially dyskinesia, in an experiment of both carotid arteries blocking in gerbil mice, a model of cerebrovascular disorders. Moreover, it was revealed that selenoprotein P could form protrusions in cultured neurocytes to thereby recover functions of injured cells. It was thus demonstrated that selenoprotein P had an activity to ameliorate neurological disturbances, especially symptoms of dyskinesia, irrespective of their causes, including ischemia/reperfusion injury.

The present invention relates to a novel pharmaceutical efficacy of selenoprotein P based on the new findings as mentioned above and an active ingredient of a medicament for ameliorating neuropathy of the present invention is selenoprotein P. More specifically, selenocysteine, a selenium-containing amino acid, contained in selenoprotein P is thought to be responsible for amelioration of neuropathy, especially dyskinesia. The present inventors have disclosed in the above patent application that a peptide fragment derived from the C-terminal of selenoprotein P, a protein from blood components, exhibited a cell death-inhibitory activity, which hitherto has not been reported. Selenocysteine contained in selenoprotein P is apparently involved in this activity. Hence, a protein and/or a series of peptides that contains selenocysteine and has a cell death-inhibitory activity can be a candidate of a medicament for ameliorating dyskinesia.

Selenium per se, as involved in the present invention, is one of essential trace elements and it is known that deficiency thereof induces a serious deficiency disease accompanied by, for instance, cardiomyopathy. It is also demonstrated that selenium is essential for survival, maintenance of life or growth of cells as can be seen from that addition of sodium selenite to culture medium is indispensable during serum-free culture. However, as will be understood from the fact that selenium compounds are designated as poisonous substance, a difference between effective and toxic amounts, i.e. a safety range of concentration, is small and hence selenium compounds used in an excess amount may be toxic to cells to induce unfavorably cell death. Acute toxic symptoms of selenium include, for example, pale face, neurological symptoms, dermatitis, and gastrointestinal disorders. It is also known that selenocystine, a dimer of selenocysteine, exhibits fairly strong toxicity when added alone to cell culture. On the contrary, no strong toxicity was observed in selenoprotein P or a peptide fragment derived from the C-terminal of selenoprotein P according to the present invention in spite of the presence of 9 to 10 selenocysteines therein. From this, selenoprotein P with the pharmaceutical efficacy according to the present invention is characteristic in that it not only contains selenocysteine but also possesses reduced toxicity. Thus, a peptide or a series of peptides of the present invention allows for providing selenium compounds that not only have reduced toxicity but also exhibit an unexpected activity to ameliorate dyskinesia.

Selenoprotein P as used herein includes any selenoprotein P in any molecular type without any restriction as far as it exhibits a desired activity to ameliorate dyskinesia, including selenoprotein P as an intact molecule or in any of other various molecule types. Among these, preferred is a peptide fragment or a series of the peptide fragments from the C-terminal of selenoprotein P. Most preferred is the peptide fragment or a series of the peptide fragments from the C-terminal of selenoprotein P that has the amino acid sequence consisting of 103 amino acid residues from the C-terminal of selenoprotein P (260th to 362nd amino acids):

```
                                          (SEQ ID NO: 3)
260Lys Arg Cys Ile Asn Gln Leu Leu Cys Lys Leu Pro

Thr Asp Ser Glu Leu Ala Pro Arg Ser Xaa Cys Cys

His Cys Arg His Leu Ile Phe Glu Lys Thr Gly Ser

Ala Ile Thr Xaa Gln Cys Lys Glu Asn Leu Pro Ser

Leu Cys Ser Xaa Gln Gly Leu Arg Ala Glu Glu Asn

Ile Thr Glu Ser Cys Gln Xaa Arg Leu Pro Pro Ala

Ala Xaa Gln Ile Ser Gln Gln Leu Ile Pro Thr Glu

Ala Ser Ala Ser Xaa Arg Xaa Lys Asn Gln Ala Lys

Lys Xaa Glu Xaa Pro Ser Asn362
``` wherein Xaa represents selenocysteine, or said amino acid sequence with one or several amino acid residues therein being deleted, substituted or added, or a partial sequence of either of the above amino acid sequences, or an amino acid sequence comprising as a part any of the above amino acid sequences.

The term "a series of the peptide fragments" as used herein refers to a group of peptide fragments with different minute structures due to presence or absence of glycosylation, difference in electric charge, diversity in fragmentation, etc., each of the peptide fragments being derived from the amino acid sequence of selenoprotein P, having at least one selenocysteine, and having said amino acid sequence with one or several amino acid residues therein being deleted, substituted or added. That is, selenoprotein P and a series of the peptide fragments according to the present invention includes any molecules that are derived from the amino acid sequence of selenoprotein P and have a cytotoxicity-inhibitory activity, including selenoprotein P as an intact molecule as well as peptide fragments from the C-terminal of selenoprotein P. The peptide fragments of the present invention may be prepared by the conventional methods using a peptide synthesizer. Alternatively, chemical compounds may also be designed by using the peptide fragments of the present invention as a lead substance.

Selenoprotein P or the peptide fragment or a series of the peptide fragments derived from said protein for use in the present invention may be prepared by any process known in the art, for example, by isolation from human blood, or by the genetic recombination technique. Selenoprotein P or the peptide fragment or a series of the peptide fragments derived from said protein for use in the present invention as an active ingredient of a medicament for ameliorating dyskinesia is rather stable to heat, a denaturing agent, a broad range of pH or protease in blood as compared to common enzymes. Thus, for purification and identification thereof, a wide variety of fractionation procedures may be applicable, including, for example, fractionations with applicable various carriers such as various chromatographic procedures such as heparin chromatography, cation exchange chromatography, anion exchange chromatography, hydrophobic chromatography, gel filtration chromatography, reverse phase chromatography, hydroxyapatite chromatography, or various affinity chromatography such as that with a column bound with an antibody, using plasma as a starting material. In addition to these, other various fractionations may also be applicable such as ammonium sulfate precipitation, molecular size fractionation with membrane, isoelectric focusing, electrophoretic fractionation, etc. A various combination of these fractionations may suitably be used to effectively fractionate selenoprotein P or the peptide fragment or a series of the peptide fragments derived from said protein. An example of preferable combinations is shown in Preparation 1.

According to the present invention, selenoprotein P or the peptide fragment or a series of the peptide fragments derived from said protein as an active ingredient may be combined with a suitable known excipient to produce a medicament for ameliorating dyskinesia. An effective dose of the medicament for ameliorating dyskinesia of the present invention may vary depending upon ages of subject, symptoms, severity, etc. and ultimately upon discretion of a physician. A pharmaceutical efficacy does not depend upon a route of administration but subcutaneous, intradermal, or intraperitoneal administration, or bolus administration within blood vessels or intravenous drip infusion is much preferred. It is also possible to administer orally or transdermally in case of peptides with a low molecular weight.

A medicament for ameliorating dyskinesia of the present invention may suitably be applied to any diseases with neurological symptoms, especially with decrease in motor function, induced by cell death or cellular degeneration of neurocytes, including, for instance, cerebrovascular disorders including cerebral infarction, cerebral hemorrhage, subarachnoid hemorrhage, multi-infarct dementia, Binswanger type leukoencephalopathy, and chronic subdural hematoma, ischemic organopathy, reperfusion injury such as graft of organ, angiopathy, neuropathy, arterial sclerosis, myocardial infarction, autoimmune diseases such as multiple sclerosis, Guillain-Barré syndrome and collagen disease, neurodegenerative diseases such as spinocerebellar degeneration, Shy-Drager syndrome, Machado-Joseph disease, myotonic dystrophy, Friedreich's syndrome, amyotrophic lateral sclerosis, Alzheimer disease, Pick disease, Huntington chorea, Parkinson disease, progressive supranuclear palsy and epilepsy, dementia or dysbasia associated with aging, or traumatic injury of spinal chord or cerebral disorders due to traffic accident. Among these, it may most preferably be applied to dyskinesia, epilepsy, motor neuron disorder, disorder associated with aging, traumatic disorder, cerebrovascular disorder, and immunopathy. A medicament for ameliorating neuropathy such as dyskinesia of the present invention comprising as an active ingredient selenoprotein P or a peptide or a series of peptides derived from said protein may be administered alone or in combination with other medical drug where synergetic effect may be expected. It may effectively be administered both for the purpose of prevention and treatment.

According to the present invention, a medicament for ameliorating neuropathy for neurodegenerative disorders induced by various causes, especially for disorders with a decrease in motor function.

The present invention is explained in more detail by means of the following Preparation and Examples which are not intended to restrict a scope of the present invention in any sense. Reagents used in the following Preparation and Examples were obtained from Wako Pure Chemical Industries, Ltd., TAKARA SHUZO CO., Ltd., Toyobo, New England BioLabs, Pharmacia, BioRad, Sigma and Gibco BRL.

Preparation 1

(Purification of Selenoprotein P Fragment Using Anti-Selenoprotein P Fragment Antibody-Bound Carrier (Anti-SeP Antibody Column))

Heparin Sepharose-binding fraction from plasma was precipitated with 2 M ammonium sulfate. The precipitate was dissolved in more than 5 volumes of 20 mM Tris buffer, pH 8.0. Selenoprotein P present in this solution was adsorbed to anti-SeP antibody column and the carrier was washed with PBS. Selenoprotein P was eluted with 20 mM citrate buffer containing 4 M urea and was adsorbed to a cation exchanger (Macroprep High S: BioRad) equilibrated with 20 mM citrate buffer. Then, gradient elution was performed with a salt concentration of sodium chloride and a fraction of selenoprotein P fragment having the cell death-inhibitory activity was recovered. At this stage, a full-length selenoprotein P could also be obtained but with a cell death-inhibitory activity per proteins being much lower than that of the fragment thereof. According to the procedures as described herein, purification may be carried out in a short time and hence selenoprotein P fragments with higher cell death-inhibitory activity per proteins could be obtained. The fragments obtained at this stage were also a fraction of a mixture containing various molecular species with varied sizes depending on the presence or absence of glycosylation, intermolecular bonding, or inner cleavage, etc. They were a group of selenoprotein P fragments that showed a size ranging from 10 to 30 kDa in electrophoresis under non-reductive condition.

EXAMPLE 1

Cytotoxicity-inhibitory Activity

Using Dami cells (described in Greenberg S. M. et al., Blood, vol. 72, p. 1968-1977 (1988)) for use in assay system for cytotoxicity-inhibitory activity, the cells were washed twice with assay medium (50% PBS/SA/0.03% HSA (manufactured by SIGMA) or SA/0.05% BSA free from fatty acid (WAKO)/4 µM long-chain polyvalent fatty acid (e.g. arachidonic acid, linoleic acid or linolenic acid)) and suspended in the same medium at $3 \times 10^4$ cells/ml. The cell suspension was added to a 96-well plate in each 200 µl for wells for sample addition or in each 100 µl for wells for serial dilution. To the wells for sample addition was added each 2 µl assay sample containing either selenoprotein P fragment prepared in Preparation 1, selenocystine, selenomethionine, Ebselen, or sodium selenite at the same concentration. After stirring, a serial dilution was made with the wells containing 100 µl cell suspension. The plate was incubated at 37° C. in $CO_2$ incubator for 4 to 5 days followed by assessment of survival of the cells.

As a result, in addition to selenoprotein P fragments purified in Preparation 1, a peptide purified therefrom under reduced condition (Lys Arg Cys Ile Asn Gln Leu Leu Cys Lys Leu Pro Thr Asp Ser Glu Leu Ala Pro Arg Ser Xaa Cys Cys His Cys Arg His Leu Ile Phe Glu Lys: SEQ ID NO: 4) proved to exhibit cytotoxicity-inhibitory activity. On the contrary, a selenoprotein P-derived peptide with no selenocysteine (Lys Arg Cys Ile Asn Gln Leu Leu Cys Lys Leu Pro Thr Asp Ser Glu Leu Ala Pro Arg Ser: SEQ ID NO: 5) proved to exhibit no cytotoxicity-inhibitory activity, demonstrating that selenocysteine is indispensable for the activity of selenoprotein P.

EXAMPLE 2

Inhibitory Effect of Selenoprotein P Fragment on Ischemia/Reperfusion Injury in Cerebral Ischemia/Reperfusion Injury Model Effect of selenoprotein P on dyskinesia induced by cerebral ischemia/reperfusion injury was assessed with a degree of paralysis using gerbil mice of 12 weeks old. The animals were systemically anesthetized by intraperitoneal injection of ketamine hydrochloride (100 mg/kg), the cervical vein was revealed by midline incision, and received 1 mg/animal of selenoprotein P fragment of the present invention via intravenous administration. After ischemia for 30 minutes or 40 minutes, the bloodstream was recovered for reperfusion. A degree of paralysis was assessed after 6 and 24 hours.

A degree of paralysis after 6 and 24 hours was assessed in accordance with the score indicated in Table 1 below.

TABLE I

| | |
|---|---|
| Normal | 0 |
| Light paralysis in the forefoot, dull movement in a posture of a bent foot | 1 |
| A little worsened paralysis in the foot, continuously turning round to one side | 2 |
| Worsened paralysis, falling down to one side | 3 |
| Still worsened paralysis, incapable of moving | 4 |
| Death | 5 |

Figure 1:
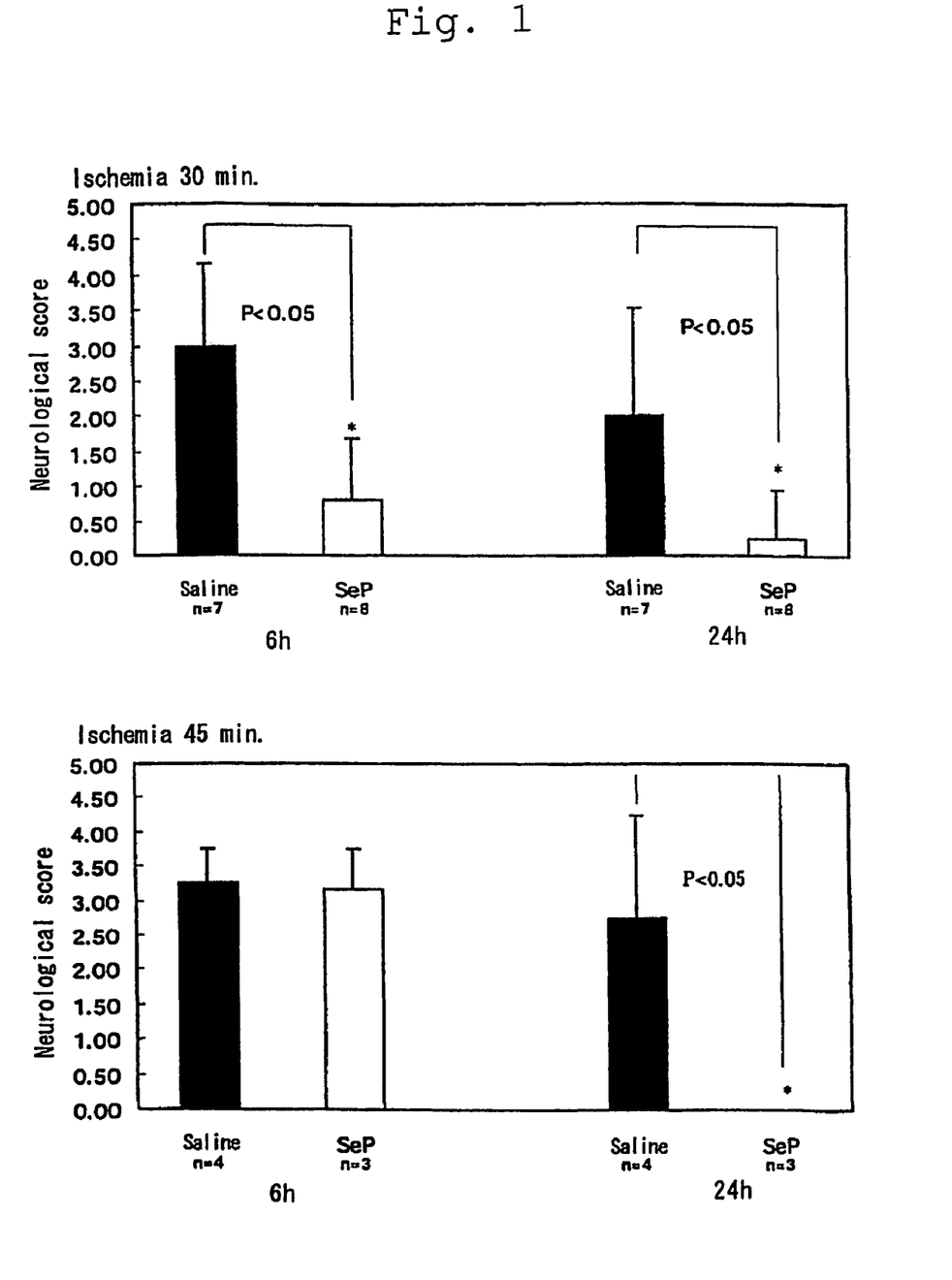
FIG. 1 shows an effect of selenoprotein P to ameliorate dyskinesia induced by blocking both carotid arteries in gerbil mice.

As shown in FIG. 1, assessing the state of paralysis after 6 and 24 hours in the 30 minutes ischemia model, the results indicated that a selenoprotein P-receiving group apparently exhibited better conditions. In case of the 45 minutes ischemia model, although no significant difference in a degree of paralysis was observed after 6 hours, much difference could be seen after 24 hours.

EXAMPLE 3

Effect of Selenoprotein P Administration on Ataxia in Klotho Mice

Effect of selenoprotein P fragment of the present invention on amelioration of decrease in motor function associated with aging was investigated using Klotho mice (Nature, 390: 45-51, 1997). Klotho mouse, an aging model mouse generated by Dr. Yohichi Nabeshima at Kyoto University, the postgraduate medical course in 1997, has an average life span of 60 days, displays retarded growth at around 20 days and in almost every case dies within around 100 days after birth. Due to Klotho gene mutation, it exhibits various abnormalities related to aging such as arterial sclerosis, emphysema, atrophoderma, atrophy of the gonad (no meiosis of ovum and sperm), neurodegeneration (drop-off of Purkinje cells in the cerebellum, ataxia), malfunction of hypophysis (decrease in growth hormone production, growth disturbance), and osteoporosis (ectopic calcification in the soft tissue or cartilage) as described in Nature, 390: 45-51. 1997. Klotho mice were obtained from CLEA Japan, Inc. with approval of Dr. Yohichi Nabeshima at Kyoto University, the postgraduate medical course.

Four Klotho mice of 4 weeks old each in two groups received weekly either selenoprotein P fragment (1.5 mg/ml) prepared in Preparation 1 dissolved in saline (300 µl) or saline alone (300 µl) via intraperitoneal injection and the conditions were observed up till 8 weeks old. As a result, no weight increase was observed in both groups where either saline alone or selenoprotein P fragment was administered and hence pathogenesis could not fundamentally be removed. However, in comparison of their behavior, the mice administered with selenoprotein P, when put on a palm, could jump off spontaneously whereas the mice administered with saline alone could not spontaneously escape, suggesting that selenoprotein P fragment may effectively ameliorate decrease in motor function.

EXAMPLE 4

Experimental Allergic Encephalomyelitis (EAE) in Mice

For investigating the effect of selenoprotein P on dyskinesia induced by immunopathy based on a degree of paralysis, an experiment was performed wherein selenoprotein P was administered to EAE mice. Female SJL/JOrlICrj of 14 weeks old (Charles River Japan, Inc.) was used as a test animal. Myelin proteolipid protein (PLP) synthetic peptide 139-151 (amino acid sequence: His Ser Leu Gly Lys Trp Leu Gly His Pro Asp Lys Phe (SEQ ID NO: 6); 25 mg/mouse) as an immunogen was intradermally administered to the mice together with Freund complete adjuvant H37Ra (400 mg/mouse) and pertussis toxin (manufactured by List Biological Laboratory; 200 ng/mouse) at two portions at the neck of tail.

Thirteen mice each in two groups received daily 0.5 mg/head of selenoprotein P via intraperitoneal administration from the day (Day 8) previous to onset of the disease till Day 13. A control group received saline via intraperitoneal administration. After onset of the disease, a degree of paralysis was daily assessed in accordance with the score indicated in Table 2 below.

TABLE 2

| | |
|---|---|
| Normal | 0 |
| Tail hanging down incompletely | 0.5 |
| Tail hanging down completely | 1 |
| Light paralysis in the hind foot | 2 |
| Medium or severe paralysis in the hind foot or light paralysis in the forefoot | 3 |
| Complete paralysis in the hind foot and/or medium to severe paralysis in the forefoot | 4 |
| Paralysis in the limbs or dying condition | 5 |
| Death | 6 |

Figure 2:
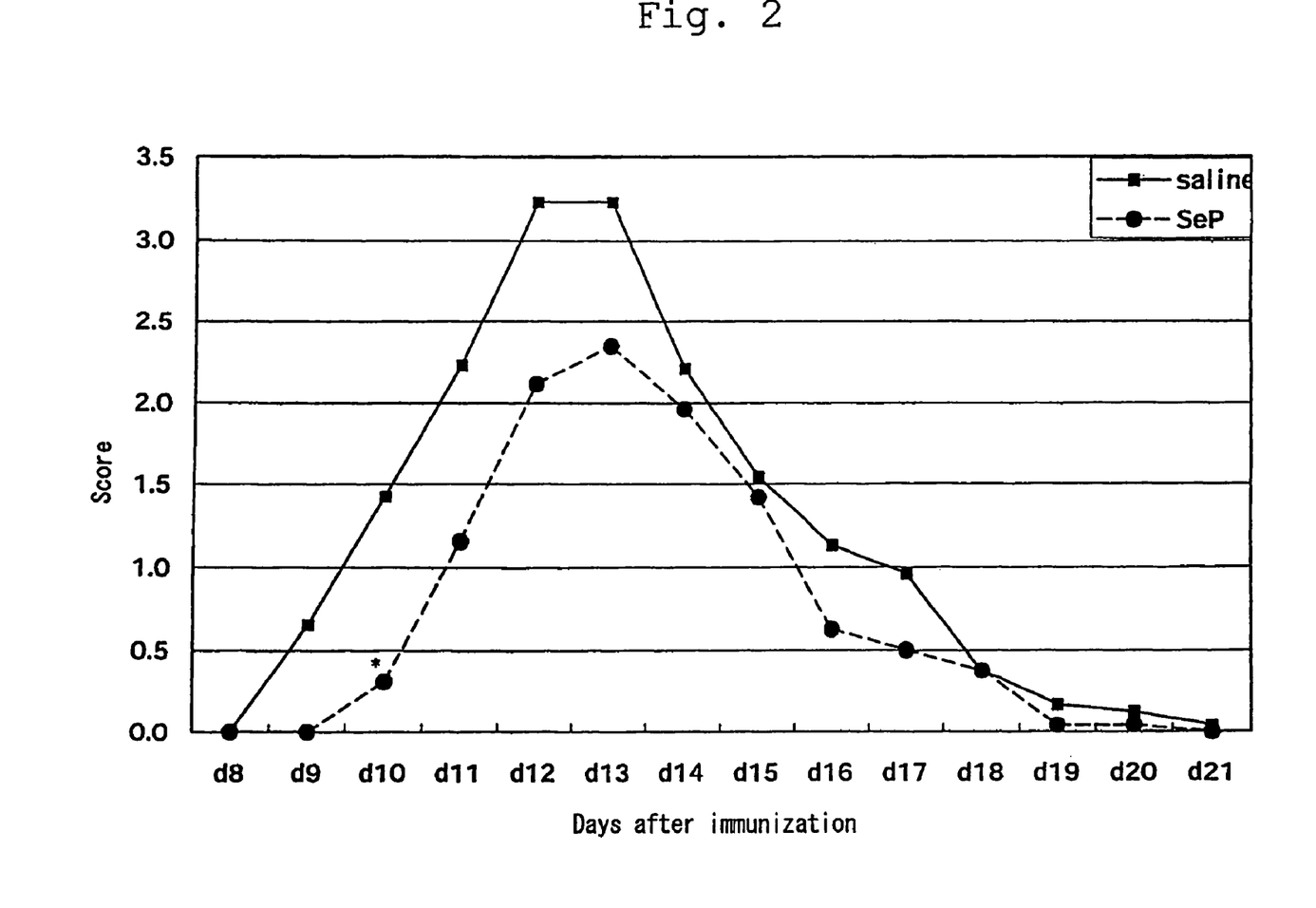
FIG. 2 shows an effect of selenoprotein P to ameliorate dyskinesia in mouse EAE.

As shown in FIG. 2, the results indicated that onset of the disease was inhibited and severity of the disease was lowered in the group administered with selenoprotein P. Besides, in comparison of a rate of onset of the disease on Day 10, 12 among the total 13 mice exhibited onset of the disease in the group administered with saline whereas only 4 among the total 13 mice did in the group administered with selenoprotein P. Thus, selenoprotein P proved to effectively inhibit onset of immunopathy and to ameliorate dyskinesia.

EXAMPLE 5

Effect of Selenoprotein P on Protrusion Formation in Cultured Human Neurocytes

NT2 (Ntera2/D1) (Pleasure, S. J. and Lee, V. M., 1993, J. Neurosci. Res. 35: 585-602) is a progenitor neurocyte derived from human teratocarcinoma and can be differentiated with retinoic acid into hNT neurocytes having the properties of the nerve in the central nervous system (Trojanowski, J. Q. et al., 1993 Exp. Neurol. 122: 283-294). Effect of selenoprotein P on protrusion formation in the hNT cells was investigated.

Both NT2 and hNT cells can be cultured in $CO_2$ incubator at 37° C. The hNT cells were prepared as follows: NT2 cells, being capable of passage culture in 10% FCS/D-MEM/F-12 medium, were first plated at $2.5 \times 10^5$ cells/ml. After 24 hours, the culture medium was replaced with D-MEM/F-12 containing 10 μM all-trans retinoic acid to initiate induction. The culture was subsequently continued for six weeks while replacing with the same medium every three days to differentiate NT2 cells into hNT cells. All the differentiated cells were recovered and expanded by 3-folds by passage culture with 10% FCS/D-MEM/F-12 medium. After 48 hours, the cells were plated at 3 to $4 \times 10^6$ cells/ml. After 48-hour culture, the culture medium was replaced with 5% FCS/D-MEM/F-12 plus mitotic inhibitor (10 μM Fluorodeoxyuridine, Uridine, 1 μM cytosine arabinoside) and culture was continued for ten days while replacing with the same medium every three days. Subsequently, the culture was treated with trypsin for a short time period and then lightly tapped to release the hNT cells which were recovered. The recovered cells were suspended in a mixed medium of an equal amount of NT2 culture supernatant (10% FCS/D-MEM/F-12 medium) and a fresh 10% FCS/D-MEM/F-12 medium. The suspension was plated on Laminin coating plate to maintain the cells. The hNT cells thus obtained were used in the following experiment.

Figure 3:
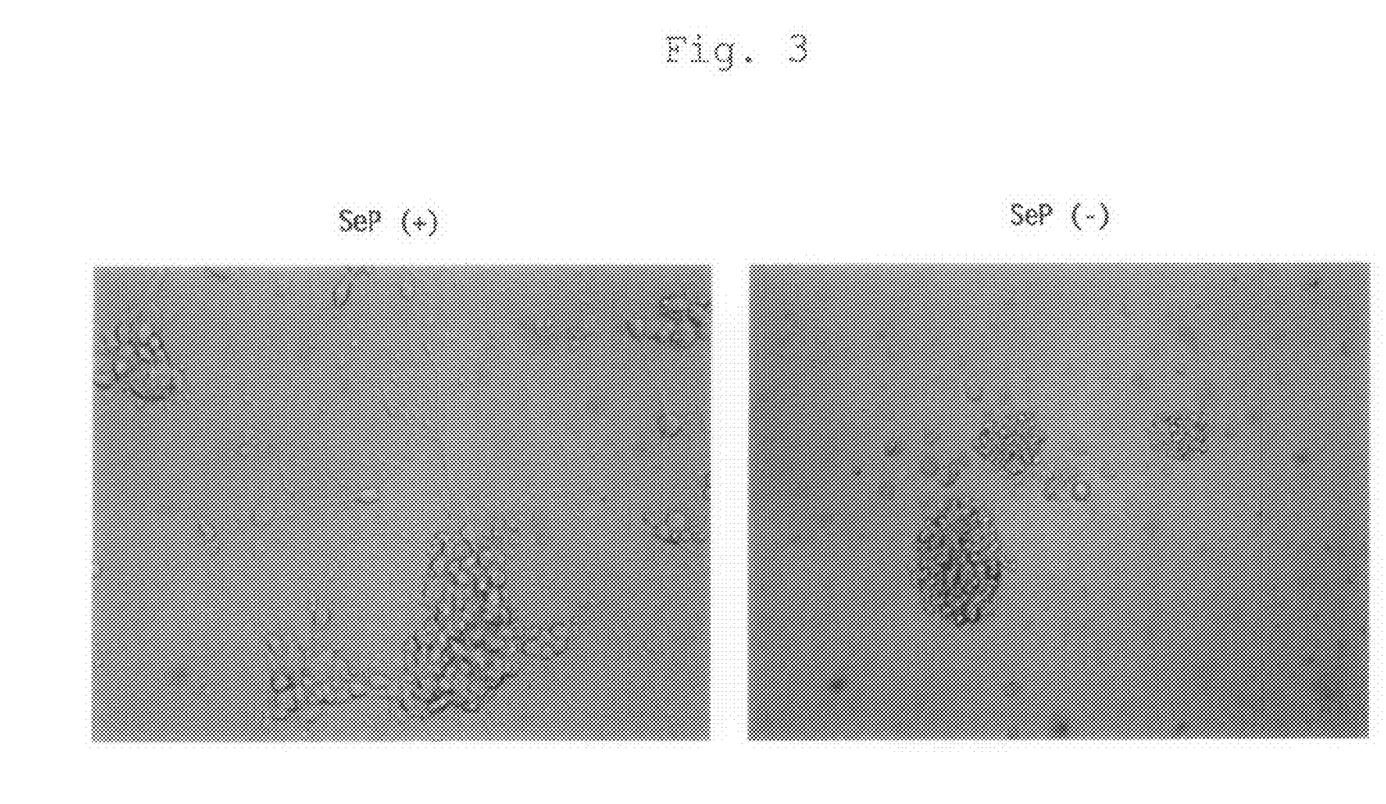
FIG. 3 is a microscopic photograph of a human neurocyte culture with (SeP(+)) or without (SeP(−)) selenoprotein P. When selenoprotein P is added, protrusion formation was observed in cultured human neurocytes.

The hNT cells were recovered by trypsin treatment, washed with a basal medium of RPMI 1640/D-MEM/F-12 (1:2:2), suspended in the same basal medium and cultured in 96-well plate at 3000 cells/well. On Day 5 to Day 7, the cells died completely. On the contrary, when selenoprotein P was added at 100 ng/ml, cell death was completely inhibited to allow the cells to survive for more than two weeks. Besides, cellular morphology was observed on Day 4 to reveal that protrusion was formed when selenoprotein P was added as shown in FIG. 3. Thus, selenoprotein P proved to effectively induce protrusion formation such as dendrite or axon in neurocytes.

The invention claimed is:,

1. A method of treating dyskinesia, said method comprising the step of administering to a subject in need thereof an effective amount of a medicament comprising a heparin sepharose-binding fraction from plasma precipitated with 2 M ammonium sulfate (Preparation 1), wherein Preparation 1 possesses a cytotoxic-inhibitory activity, and wherein selenocysteine is an amino acid present in Preparation 1 wherein the dyskinesia is associated with a disease or condition selected from the group consisting of:

a) a cerebrovascular disorder selected from the group consisting of Binswanger type leukoencephalopathy, chronic subdural hematoma, and angiopathy;

b) an autoimmune disease;

c) a traumatic disorder selected from the group consisting of a traumatic injury of the spinal cord and a cerebral disorder due to a traffic accident;

d) spinocerebellar degeneration;

e) Shy-Drager syndrome;

f) Machado-Joseph disease;

g) myotonic dystrophy;

h) Friedrich's ataxia;

i) amyotrophic lateral sclerosis;

j) Pick disease;

k) Huntington chorea;

l) progressive supranuclear palsy; and m) epilepsy.

2. The method according to claim 1, wherein said Preparation 1 comprises the amino acid sequence as set forth in SEQ ID NO:3 and possesses a cytotoxicity-inhibitory activity.

3. The method according to claim 1, wherein said Preparation 1 comprises peptides having amino acid sequences of the formula (I):

Lys Arg Cys Ile Asn Gln Leu Leu Cys Lys Leu Pro Thr Asp Ser Glu Leu Ala Pro Arg Ser Xaa Cys Cys His Cys Arg His Leu (SEQ ID NO: 1) and/or the formula (II): Thr Gly Ser Ala Ile Thr Xaa Gln Cys Lys Glu Asn Leu Pro Ser Leu Cys Ser Xaa Gln Gly Leu Arg Ala Glu Glu Asn Ile (SEQ ID NO: 2) wherein Xaa represents selenocysteine.

4. The method according to claim 2, wherein said Preparation 1 comprises peptides having amino acid sequences of the formula (I):

Lys Arg Cys Ile Asn Gln Leu Leu Cys Lys Leu Pro Thr Asp Ser Glu Leu Ala Pro Arg Ser Xaa Cys Cys His Cys Arg His Leu (SEQ ID NO: 1) and/or the formula (II): Thr Gly Ser Ala Ile Thr Xaa Gln Cys Lys Glu Asn Leu Pro Ser Leu Cys Ser Xaa Gln Gly Leu Arg Ala Glu Glu Asn Ile (SEQ ID NO: 2) wherein Xaa represents selenocysteine.

5. The method according to claim 1, wherein the dyskinesia is associated with a cerebrovascular disorder selected from the group consisting of Binswanger type leukoencephalopathy, chronic subdural hematoma, and angiopathy.

6. The method according to claim 1, wherein the dyskinesia is associated with a disease or condition selected from the group consisting of spinocerebellar degeneration, Shy-Drager syndrome, Machado-Joseph disease, myotonic dystrophy, Friedreich's syndrome, amyotrophic lateral sclerosis, Pick disease, Huntington chorea, progressive supranuclear palsy, and epilepsy.

7. The method according to claim 1, wherein the dyskinesia is associated with a traumatic disorder selected from the group consisting of a traumatic injury of the spinal cord and a cerebral disorder due to a traffic accident.

8. The method according to claim 6, wherein the dyskinesia is associated with epilepsy.

9. The method according to claim 1, wherein the dyskinesia is associated with an autoimmune disease selected from the group consisting of multiple sclerosis, Guillain-Barre syndrome and collagen disease.

* * * * *

SEQUENCE LISTING

```
<160> NUMBER OF SEQ ID NOS: 6

<210> SEQ ID NO 1
<211> LENGTH: 29
<212> TYPE: PRT
<213> ORGANISM: Homo sapiens
<220> FEATURE:
<221> NAME/KEY: misc_feature
<222> LOCATION: (22)..(22)
<223> OTHER INFORMATION: Xaa represents selenocysteine

<400> SEQUENCE: 1

Lys Arg Cys Ile Asn Gln Leu Leu Cys Lys Leu Pro Thr Asp Ser Glu
1               5                   10                  15

Leu Ala Pro Arg Ser Xaa Cys Cys His Cys Arg His Leu
            20                  25

<210> SEQ ID NO 2
<211> LENGTH: 28
<212> TYPE: PRT
<213> ORGANISM: Homo sapiens
<220> FEATURE:
<221> NAME/KEY: misc_feature
```

```
<222> LOCATION: (7)..(7)
<223> OTHER INFORMATION: Xaa represents selenocysteine
<220> FEATURE:
<221> NAME/KEY: misc_feature
<222> LOCATION: (19)..(19)
<223> OTHER INFORMATION: Xaa represents selenocysteine

<400> SEQUENCE: 2

Thr Gly Ser Ala Ile Thr Xaa Gln Cys Lys Glu Asn Leu Pro Ser Leu
1               5                   10                  15

Cys Ser Xaa Gln Gly Leu Arg Ala Glu Glu Asn Ile
            20                  25

<210> SEQ ID NO 3
<211> LENGTH: 103
<212> TYPE: PRT
<213> ORGANISM: Homo sapiens
<220> FEATURE:
<221> NAME/KEY: misc_feature
<222> LOCATION: (22)..(22)
<223> OTHER INFORMATION: Xaa represents selenocysteine
<220> FEATURE:
<221> NAME/KEY: misc_feature
<222> LOCATION: (40)..(40)
<223> OTHER INFORMATION: Xaa represents selenocysteine
<220> FEATURE:
<221> NAME/KEY: misc_feature
<222> LOCATION: (52)..(52)
<223> OTHER INFORMATION: Xaa represents selenocysteine
<220> FEATURE:
<221> NAME/KEY: misc_feature
<222> LOCATION: (67)..(67)
<223> OTHER INFORMATION: Xaa represents selenocysteine
<220> FEATURE:
<221> NAME/KEY: misc_feature
<222> LOCATION: (74)..(74)
<223> OTHER INFORMATION: Xaa represents selenocysteine
<220> FEATURE:
<221> NAME/KEY: misc_feature
<222> LOCATION: (89)..(89)
<223> OTHER INFORMATION: Xaa represents selenocysteine
<220> FEATURE:
<221> NAME/KEY: misc_feature
<222> LOCATION: (91)..(91)
<223> OTHER INFORMATION: Xaa represents selenocysteine
<220> FEATURE:
<221> NAME/KEY: misc_feature
<222> LOCATION: (98)..(98)
<223> OTHER INFORMATION: Xaa represents selenocysteine
<220> FEATURE:
<221> NAME/KEY: misc_feature
<222> LOCATION: (100)..(100)
<223> OTHER INFORMATION: Xaa represents selenocysteine

<400> SEQUENCE: 3

Lys Arg Cys Ile Asn Gln Leu Leu Cys Lys Leu Pro Thr Asp Ser Glu
1               5                   10                  15

Leu Ala Pro Arg Ser Xaa Cys Cys His Cys Arg His Leu Ile Phe Glu
                20                  25                  30

Lys Thr Gly Ser Ala Ile Thr Xaa Gln Cys Lys Glu Asn Leu Pro Ser
            35                  40                  45

Leu Cys Ser Xaa Gln Gly Leu Arg Ala Glu Glu Asn Ile Thr Glu Ser
        50                  55                  60

Cys Gln Xaa Arg Leu Pro Pro Ala Ala Xaa Gln Ile Ser Gln Gln Leu
65                  70                  75                  80

Ile Pro Thr Glu Ala Ser Ala Ser Xaa Arg Xaa Lys Asn Gln Ala Lys
                85                  90                  95

Lys Xaa Glu Xaa Pro Ser Asn
            100
```

```
<210> SEQ ID NO 4
<211> LENGTH: 33
<212> TYPE: PRT
<213> ORGANISM: Homo sapiens
<220> FEATURE:
<221> NAME/KEY: misc_feature
<222> LOCATION: (22)..(22)
<223> OTHER INFORMATION: Xaa represents selenocysteine

<400> SEQUENCE: 4

Lys Arg Cys Ile Asn Gln Leu Leu Cys Lys Leu Pro Thr Asp Ser Glu
1               5                   10                  15

Leu Ala Pro Arg Ser Xaa Cys Cys His Cys Arg His Leu Ile Phe Glu
            20                  25                  30

Lys

<210> SEQ ID NO 5
<211> LENGTH: 21
<212> TYPE: PRT
<213> ORGANISM: Homo sapiens

<400> SEQUENCE: 5

Lys Arg Cys Ile Asn Gln Leu Leu Cys Lys Leu Pro Thr Asp Ser Glu
1               5                   10                  15

Leu Ala Pro Arg Ser
            20

<210> SEQ ID NO 6
<211> LENGTH: 13
<212> TYPE: PRT
<213> ORGANISM: Artificial Sequence
<220> FEATURE:
<223> OTHER INFORMATION: Myelin proteolipid protein (PLP) synthetic
      peptide 139-151

<400> SEQUENCE: 6

His Ser Leu Gly Lys Trp Leu Gly His Pro Asp Lys Phe
1               5                   10
```